(12) United States Patent
Excoffier et al.

(10) Patent No.: US 7,275,682 B2
(45) Date of Patent: Oct. 2, 2007

(54) SAMPLE IDENTIFICATION UTILIZING RFID TAGS

(75) Inventors: Jean-Louis Excoffier, Richmond, CA (US); Leslie E. Ehrlich, Walnut Creek, CA (US)

(73) Assignee: Varian, Inc., Palo Alto, CA (US)

( * ) Notice: Subject to any disclaimer, the term of this patent is extended or adjusted under 35 U.S.C. 154(b) by 250 days.

(21) Appl. No.: 11/088,539

(22) Filed: Mar. 24, 2005

(65) Prior Publication Data

US 2006/0213964 A1 Sep. 28, 2006

(51) Int. Cl.
*G06K 19/06* (2006.01)
(52) U.S. Cl. .................................. 235/375; 235/492
(58) Field of Classification Search ............... 235/385, 235/375, 462.01, 381, 492, 449; 435/6, 7.1, 435/287.2; 436/46, 48; 422/102, 63
See application file for complete search history.

(56) References Cited

U.S. PATENT DOCUMENTS

| | | | |
|---|---|---|---|
| 4,528,159 | A | 7/1985 | Liston |
| 5,104,621 | A | 4/1992 | Pfost et al. |
| 5,460,783 | A | 10/1995 | Hautea et al. |
| 5,650,122 | A | 7/1997 | Harris et al. |
| 6,241,947 | B1 | 6/2001 | Komatsu et al. |
| 6,602,206 | B1 | 8/2003 | Niermann et al. |
| 2003/0087446 | A1* | 5/2003 | Eggers .................. 436/48 |
| 2003/0174046 | A1 | 9/2003 | Abrams |
| 2004/0100415 | A1* | 5/2004 | Veitch et al. ............ 343/850 |
| 2004/0101966 | A1* | 5/2004 | Davis et al. ............. 436/43 |
| 2004/0219602 | A1* | 11/2004 | Carlson et al. .......... 435/7.1 |
| 2004/0265187 | A1 | 12/2004 | Davin |
| 2005/0169733 | A1* | 8/2005 | Drynkin et al. .......... 414/404 |
| 2005/0205673 | A1* | 9/2005 | Morris et al. ............ 235/385 |
| 2006/0199196 | A1* | 9/2006 | O'Banion et al. ........ 435/6 |

FOREIGN PATENT DOCUMENTS

EP 1 388 810 A 2/2004

OTHER PUBLICATIONS

Publication entitled "Supply-Chain Technology" published Jun. 2003 by Bear, Stearns & Co., Inc.
Giger. J: Jan. 31, 2005 Lab Automation: Maxell Partners with ABgene and Micronic at Lab Automation 2005 to Showcase First Demonstration of RFID Technology in the Laboratory, retrieved from internet: www.maxwell-usa.com/rfid/LabAutomation2005.doc.

* cited by examiner

*Primary Examiner*—Thien Minh Le
(74) *Attorney, Agent, or Firm*—Bella Fishman; David Gloekler

(57) ABSTRACT

A sample container may include an open end, a closure member, a cap, and an RFID tag. The RFID tag may be positioned near the open end and includes a code uniquely identifying an analytical sample contained in the container structure. A sample handling apparatus may operate with one or more sample containers. The sample handling apparatus may include a robotic assembly for moving a sample probe device and a sample probe supported by a guide of the sample probe device. An RF transceiver antenna may be mounted to the guide for communicating with the RFID tag of the sample container. The sample probe device is moved into proximity with a sample container to read a code stored by an RFID tag attached to the sample container, whereby a sample contained in the sample container can be uniquely identified. The code can be associated with additional information relating to the identified sample.

25 Claims, 5 Drawing Sheets

SAMPLE IDENTIFICATION UTILIZING RFID TAGS

FIELD OF THE INVENTION

The present invention relates generally to sample handling, such as the handling of one or more individual samples in conjunction with analytical processes. More particularly, the present invention relates to the use of radio-frequency (RF) energy to uniquely identify individual samples and/or containers in which the samples reside.

BACKGROUND OF THE INVENTION

In many processes for analyzing samples, particularly in batch and serial processes where several samples are involved, it is desirable to improve throughput by providing a greater degree of automated control over various stages of the sample handling, preparation, and analysis processes and by providing better management of sample-related data. In one aspect, instrumentation for the handling, preparation and analysis of samples has become more automated. For instance, automated sample handling systems have been developed that include one or more trays holding arrays of vials, test tubes, or multi-well plates containing small quantities of liquid samples. These systems typically include a sampling needle that can be programmed to move to each vial in order to dispense samples into the vials or aspirate samples from the vials. Alternatively, the vials or trays holding the vials may be moved to a sampling needle or other component of the sample handling system. In another aspect, steps have been taken to improve the identification of individual samples. Improvements in sample identification have primarily been made through the utilization of barcode scanning systems. Barcode scanning systems employ an optical barcode scanner that reads a barcode printed on a label. The barcode consists of a combination of dark parallel bars and light spaces between the bars. The barcode scanner reads the barcode by directing a beam of light at the barcode. Because the dark bars of the barcode absorb light and the light spaces reflect light, a detector in the barcode scanner can receive the reflected light signals and convert them into electrical signals, which thereafter can be recognized by electronic means as characters. Barcode labels have been applied to vials and, in the case of multi-well plates, a single barcode label has been applied to a plate.

While barcode systems and other optical techniques may be useful in such applications as the tracking of consumer goods, these types of systems present problems when applied to procedures for handling small liquid-phase samples in conjunction with analytical techniques. The information represented by a barcode is quite limited and fixed. The barcode typically constitutes a short series of characters such as those corresponding to the well-known Uniform Product Code (UPC). Due to the brevity of these character sets, the barcode is capable of identifying only the type of sample or the tray or group of samples of which the sample is a part. When a large number of individual samples are to be handled and analyzed, each of which may be different from the others in terms of composition or other parameters, there are not enough characters in a barcode to adequately distinguish one given sample as being unique from another sample. Even if a barcode were to be employed to uniquely identify a sample as being, for example, Sample #1, that same barcode cannot be used to provide any additional information about that particular sample.

Moreover, because a barcode system depends on optics, it is orientation-sensitive; that is, there are only a finite range of angles between a barcode and a barcode scanner over which optical communication will be successful. When applied to sample handling and analysis systems, the barcode system often requires that several barcode scanners be located at various points along the system in order to adequately track the sample, or that a given barcode-containing vial be transported to a single barcode scanner. Additionally, again due to the use of optics, a barcode-containing vial must be precisely positioned in relation to a barcode scanner to ensure that no other object will interfere with the light path, including neighboring vials. Another related problem stems from the fact that an optical path is easily modified by the presence of substances commonly encountered in sample handling. The smearing of the printed barcode through contact with a researcher or an object, the marring or degradation of the barcode by solvents or other substances, or simply the obstructive presence of fluids or particles on the barcode, all may destroy the ability of the barcode to be accurately read by a barcode scanner.

In view of the foregoing, it would be advantageous to provide a means for uniquely identifying vials and other types of sample containers without the problems attending barcode technology and other known techniques employed in conjunction with sample preparation, handling, and/or analysis. The ability to read an identification code as the vial is accessed for sampling or mixing operations, without moving the vial to another position, would also present significant advantages, in terms of time and chain of custody-type concerns.

SUMMARY OF THE INVENTION

To address the foregoing problems, in whole or in part, and/or other problems that may have been observed by persons skilled in the art, the present disclosure provides apparatus, devices, and methods for uniquely identifying individual analytical samples, as described by way of example in implementations set forth below.

According to one implementation, a sample handling apparatus is provided. The sample handling apparatus comprises a robotic assembly comprising a movable member, a sample probe device mounted to and movable with the movable member, and an RF transceiver antenna. The sample probe device comprises a sample probe guide and a sample probe extending through the guide. The RF transceiver antenna is mounted to the movable member.

According to another implementation, the sample handling apparatus further comprises a sample container that is accessible by the sample probe. The sample container comprises a first structure including an open end enclosing an interior, a second structure mounted to the first structure at the open end, and an RFID tag positioned with the second structure. The RF transceiver antenna is movable into proximity with the RFID tag for communicating therewith.

According to another implementation, a sample handling apparatus comprises a robotic assembly comprising a movable member, and a sample probe device mounted to and movable with the movable member. The sample probe device comprises a sample probe. The sample handling apparatus further comprises means for reading a code stored by an RFID tag, the code comprising information identifying an analytical sample contained in a sample container accessible by the sample probe.

According to another implementation, a method for uniquely identifying an analytical sample is provided.

According to the method, a sample probe device is moved into proximity with a sample container. The sample probe device comprises an RF transceiver antenna and a sample probe. The RF transceiver antenna is employed to read a code stored by an RFID tag attached to the sample container, whereby a sample contained in the sample container can be identified.

According to another implementation, the method further comprises, after reading the code, associating the code with information relating to the identified sample.

According to another implementation, a sample container is provided. The sample container comprises a container structure including an open end, a closure member mounted to the container structure at the open end, a cap mounted to the container structure at the open end, and a radio-frequency identification (RFID) tag. The closure member isolates the interior of the container structure from an environment external to the container structure. The cap includes an aperture providing external access to the closure member. The RFID tag is positioned near the open end and includes a code uniquely identifying an analytical sample contained in the container structure.

According to another implementation, a sample container comprises a first structure including an open end enclosing an interior, a second structure mounted to the first structure at the open end, and means positioned with the second structure for storing a code uniquely identifying a sample contained in the first structure and transmitting an RF signal bearing the code in response to activation by an RF transceiving device.

DETAILED DESCRIPTION OF THE INVENTION

In general, the term "communicate" (for example, a first component "communicates with" or "is in communication with" a second component) is used herein to indicate a structural, functional, mechanical, electrical, optical, magnetic, ionic or fluidic relationship between two or more components or elements. As such, the fact that one component is said to communicate with a second component is not intended to exclude the possibility that additional components may be present between, and/or operatively associated or engaged with, the first and second components.

The subject matter disclosed herein generally relates to the handling of one or more individual samples as, for instance, may be performed as part of or in preparation for a sample analysis process. The subject matter provides for the unique identification of individual samples so that one sample may be readily distinguished from another sample and that once identified, the identity of the sample may be correlated with additional information uniquely pertaining to that sample. Accordingly, systems, apparatus, and methods disclosed herein may be particularly beneficial in applications entailing the analysis of several individual samples simultaneously or serially in a given test run, where one or more samples may be different from other samples, and where one or more components of the system or apparatus may be partially or fully automated. The approach toward identification of samples disclosed herein makes use of RF energy and therefore does not rely on optical energy and is not limited by optics-related problems. Examples of implementations of apparatus, systems, devices, and/or related methods for sample identification and sample handling are described in more detail below with reference to FIGS. 1-5.

Figure 1:
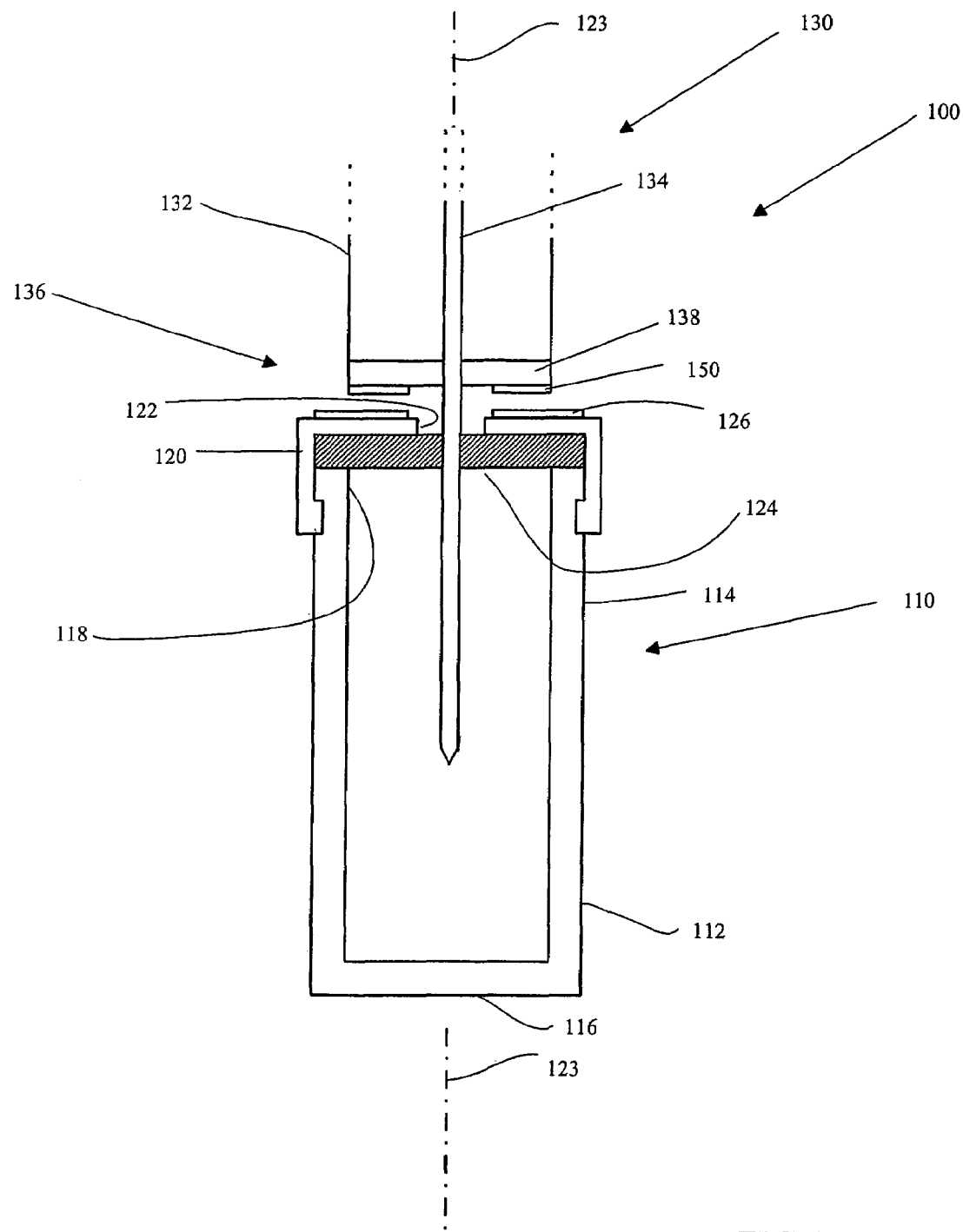
FIG. 1 is a front elevation view of a cross-section of a sample container and sample probe device provided in accordance with an example of one implementation.

FIG. 1 is a front elevation view of a cross-section of a sample handling apparatus or system 100 provided with sample identification functionality in accordance with an example of one implementation. Sample handling apparatus 100 operates in conjunction with a sample container 110. In some implementations, sample handling apparatus 100 may be considered as comprising sample container 110. That is, in some implementations, sample container 110 may be considered as being part of sample handling apparatus 100.

Sample container 110 may be any container suitable for containing an analytical sample, particularly a liquid-phase or multi-phase sample for which one or more quantitative and/or qualitative analyses are desired. Examples of sample containers 110 include, but are not limited to, vials, test tubes, curvets, wells, flow-through cells, and the like. In the example illustrated in FIG. 1, sample container 110 includes a first structure or container structure 112 that defines the interior of sample container 110 in which an individual sample may reside. Container structure 112 may include one or more side walls 114, a closed bottom end 116, and an open top end 118. Typically, container structure 112 is generally cylindrical in shape, but in alternative implementations may have a polygonal profile of any suitable type. Container structure 112 may be constructed from glass, plastic, or any other material suitable for containing analytical samples. Container structure 112 may include an end member or cap 120 mounted to a surface of container structure 112 at its open end 118. Cap 120 may be attached to container structure 112 by crimping, threading, or any other suitable means. In some implementations, cap 120 includes an aperture 122 that typically is centrally located relative to a central, longitudinal axis 123 of container structure 112.

Generally, no limitation is placed on the size of container structure 112 or its capacity for holding a volume of sample material. In some implementations, container structure 112 may enclose an interior that has a volume ranging from approximately 0.1 mL to approximately 1000 mL. In other implementations, the volume may range from approximately 0.1 mL to approximately 100 mL. In other implementations, the volume may range from approximately 1 mL to approximately 50 mL. In other implementations, the volume may range from approximately 2 mL to approximately 20 mL.

Container structure 112 may also include a closure member 124, for example a septum or plug, that is attached or mounted to container structure 112 so as to close off its open end 118 and thereby isolate or seal the interior of sample container 110 from the ambient environment As appreciated by persons skilled in the art, closure member 124 may be composed of a resilient or deformable material that enables closure member 124 to perform its isolating function, as well as to be pierced by a needle without impairing its ability to provide isolation. In some implementations, closure member 124 is secured to container structure 112 by press-fining, which may be facilitated by the installation of cap 120 onto container structure 112. The aperture 122 of cap 120 provides external access to closure member 124 so that a needle or the like may be inserted through closure member 124 and into container structure 112. In some implementations in which closure member 124 is not needed, sample container 110 is employed in an open mode, in which case the aperture 122 of cap 120 provides direct access to the interior of sample container 110.

In some implementations, container structure 112 may have open ends at both the top and the bottom, and closure members and/or caps at both the top and the bottom. Examples of these container structures include purge and trap vials commercially available from Varian, Inc., Palo Alto, Calif., and typically are employed for soil analysis or other types of environmental analysis. In some implementations, sample container 110 may include a magnetic stirring or agitating element such as a bar or bead.

For purposes of the present disclosure, no limitation is placed on the composition of the sample or its properties (for example, molecular weight, polarity or non-polarity, ionic, volatility, temperature, or the like), or on the manner in which the sample is provided to sample container 110. In a typical implementation, the sample provided to sample container 110 is predominantly a liquid but in other implementations may be a multi-phase mixture. For example, the sample may be a solution, emulsion, suspension or mixture in which analyte components (for example, molecules of interest) are initially dissolved in one or more solvents or carried by other types of components. In some implementations, particularly those associated with headspace sampling techniques and which in turn may be associated with gas chromatography (GC) or solid-phase micro-extraction (SPME), sample container 110 may contain a vapor above a liquid or solid. In such techniques, it is the vapor that typically is sampled, and hence the vapor may be considered to be the sample or part of the sample. Accordingly, terms such as "sample" or "sample material" as used herein are not limited by any particular phase, form, or composition. Generally, however, the sample contains analytes of the type that are amenable to qualitative and/or quantitative instrumental techniques of analytical chemistry such as, for example, the various types of chromatography, dissolution, mass spectrometry, spectroscopy, nuclear magnetic resonance (NMR) spectrometry or imaging, calorimetry, and the like. The sample may be dispensed into sample container 110 or removed from sample container 110 either manually or by automated means.

In accordance with implementations described in this disclosure, sample container 110 includes a second structure that supports a device for storing information uniquely pertaining to the sample contained within sample container 110. This device, which may be referred to as a radio-frequency identification (RFID) tag 126, transponder, smart label, or smart chip, is described in more detail below. In the example illustrated in FIG. 1, RFID tag 126 is positioned with cap 120 such that cap 120 serves as the second structure supporting RFID tag 126. In other implementations, as can be readily appreciated from FIG. 1, RFID tag 126 may alternatively be positioned with closure member 124 such that closure member 124 serves as the second structure supporting RFID tag 126. RFID tag 126 may be positioned with cap 120 or closure member 124 in any suitable fixed manner. As examples, RFID tag 126 may be attached or mounted to cap 120 or closure member 124 through the use of an adhesive backing or glue, or may be integrated with cap 120 or closure member 124 by any suitable fabrication process. In other implementations, RFID tag 126 may be attached directly to container structure 112. In other implementations, RFID tag 126 may be attached directly to container structure 112 at or near the bottom of container structure 112 instead or at or near open end 118 at the top. For instance, RFID tag 126 may be attached to a side wall 114 or centered at closed bottom end 116 of container structure 112. In implementations where a multi-well plate is provided that contains a plurality of wells corresponding to an array of container structures 112, a plurality of RFID tags 126 may be respectively positioned at the centers of corresponding bottom ends 116. In still other implementations in which container structure 112 has opposing open ends and closure members and/or caps at both the top and the bottom, RFID tag 126 may be attached or mounted to the closure member or the cap that is located at the bottom of container structure 112, in which case the second structure would correspond to the closure member or the cap located at the bottom.

Sample handling apparatus 100 may be any apparatus that can function to transfer a sample to and/or from sample container 110, and/or transfer a probe of any suitable type into and/or out from sample container 110 such as, for example, a sample-absorbing wick or fiber, an optical probe, a temperature probe, a stirrer or agitator, or the like. In the present context, the term "transfer" is intended to encompass dispensing or loading a sample (or a portion of a sample) into sample container 110, aspirating or removing a sample (or a portion of a sample) from sample container 110, or both, or inserting a probe into sample container 110 or removing a probe from sample container 110. For any of these purposes, sample handling apparatus 100 includes a sample transfer or probe device 130 that is movable toward and away from sample container 110, and hence toward and away from RFID tag 126. Accordingly, the term "sample probe device" may encompass a sample transfer device or a probe transfer device. The mobility of sample probe device 130 may be fully automated or semi-automated. Moreover, one or more components of sample probe device 130 may be movable in one, two, or three dimensions. The portion of sample probe device 130 illustrated in FIG. 1 may represent a movable member 132, such as a probe head or carriage or a needle-mounting head, provided with sample handling apparatus 100. As appreciated by persons skilled in the art, a movable member 132 of this type may be driven by components provided with sample handling apparatus 100 such as, for example, a robotic assembly or one or more motors, actuators, linkages, guide means, and the like.

Sample probe device 130 may also include a sample probe 134 that may be adapted to carry out one or more functions or operations. In the example illustrated in FIG. 1, sample probe device 130 is adapted for handling liquid samples and thus may be characterized as a sample transfer device. Accordingly, the sample probe 134 associated with sample probe device 130 may be provided in the form of a sample conduit through which a sample may be transferred to or from sample container 110. Sample probe 134 may be supported by or attached to movable member 132. Examples of a sample probe 134 include, but are not limited to, a capillary, needle, tube, pipe, pipette, cannula, hollow probe, sensing, detecting or measuring instrument (for example, a dip probe or camera), stirrer, and the like. In some implementations, sample probe device 130 is able to insert sample probe 134 into sample container 110. In implementations where sample container 110 includes closure member 124, sample probe 134 may be structured so as to be able to pierce through and penetrate closure member 124 to access the interior of sample container 110. Sample probe 134 extends, or is extendable, out from a lower end region 136 of sample probe device 130. Sample probe device 130 may include a sample probe guide 138 positioned at lower end region 136 to support and/or guide sample probe 134. Sample probe 134 may be fixed relative to sample probe device 130 or to at least that portion of sample probe device 130 shown in FIG. 1, in which case sample probe device 130 may be lowered toward sample container 110 in order to insert sample probe 134 into sample container 110. Alternatively, sample probe 134 may be movable relative to sample probe device 130 for extending sample probe 134 into and out from sample container 110. In either case, sample probe guide 138 maintains sample probe 134 in a proper position or alignment with respect to lower end region 136.

In some implementations, sample probe 134 may be a hollow sheath that contains a sample-absorbing fiber. This fiber may be extended into a liquid sample contained in sample container 110 (for example, in SPME techniques) or into a vapor contained in sample container 110 above the liquid or solid (for example, in headspace SPME techniques). The fiber absorbs compounds of interest from the liquid or vapor and is then retracted into the sheath. The sheath is then drawn out from sample container 110. The sheath may function as a needle so that it is able to pierce a closure member 124 while protecting the fiber. In other implementations, sample probe 134 may be adapted to perform some type of analysis, detection, or measurement. Accordingly, sample probe 134 may be, for example, an optical probe or a temperature-sensing probe. Alternatively, sample probe 134 may also include the afore-mentioned sheath that is adapted for piercing a closure member 124 while protecting this type of probe.

Sample probe device 130 further includes a radio-frequency (RF) transceiver antenna 150 for communicating with RFID tag 126 of sample container 110. In some implementations, RF transceiver antenna 150 advantageously is positioned at or near a lowermost part of lower end region 136 of sample probe device 130 for communicating with RFID tag 126 at close range, and in some implementations may even contact RFID tag 126 although contact is not required. This configuration ensures that RF transceiver antenna 150 will come into close proximity with RFID tag 126 (for example, a few millimeters) when sample probe device 130 is moved into position over sample container 110. As appreciated by persons skilled in the art, the sensitivity of RF transceiver antenna 150 and/or the electronics with which it communicates can be adjusted for close-range communication with RFID tag 126. In the present context, this configuration ensures that RF transceiver antenna 150 is able to discriminate the RFID tag 126 of one sample container 110 from the RFID tag 126 of another, nearby sample container 110. That is, when sample probe device 130 is positioned over sample container 110, RF transceiver antenna 150 should be able to read the RFID tag 126 of that particular sample container 110 and not an RFID tag 126 provided with any other sample container 110. Moreover, RF transceiver antenna 150 may be utilized to sense whether a particular sample container 110 is missing from an array of sample containers or contains no RFID tag 126. For any of these purposes, as shown in the example illustrated in FIG. 1, RF transceiver antenna 150 may be mounted to sample probe guide 138.

In some implementations, also shown in the cross-sectional view of FIG. 1, RF transceiver antenna 150 and RFID tag 126 may be substantially centered about sample probe 134 and/or central longitudinal axis 123 of sample container 110 so as to be generally aligned with each other. For instance, both RF transceiver antenna 150 and RFID tag 126 may comprise respective annular RF transmitting components such as conductive loops that are generally aligned with each other. These loops may be positioned concentrically relative to sample probe 134 and/or central longitudinal axis 123 of sample container 110, and lie along planes parallel to the top of sample container 110. Implementations utilizing conductive loops may enhance the selectivity with which RF transceiver antenna 150 is able to read RFID tag 126, particularly at certain frequencies.

Generally, RFID tag 126 may be any device capable of storing data and transmitting the data via an RF carrier signal in response to a query from a suitable reader, such as an RF-based query transmitted by an RF transceiver antenna 150. For example, RFID tag 126 may be realized by forming an integrated circuit on a suitable substrate such as a silicon chip. The chip in turn may be provided on a flexible substrate such as a label or adhesive sticker. In some implementations, RFID tag 126 may also include a small, typically flexible antenna interconnected to the integrated circuit or chip to enable RFID tag 126 to transmit RF signals to a suitable reader such as RF transceiver antenna 150. In other implementations, electrical contacts or interconnects provided with RFID tag 126 may serve the same purpose as an antenna in which case a discrete antenna need not be fabricated with RFID tag 126.

RFID tag 126 may be passive, active, or semi-passive. As can be appreciated by persons skilled in the art, a passive RFID tag 126 does not require a power source for its operation. A passive RFID tag 126 can absorb some of the electromagnetic energy from a signal sent by RF transceiver antenna 150 and reflect the energy as an RF return signal that carries the coded information stored in its memory. For example, an RF scan transmitted by RF transceiver antenna 150 may induce electrical current in the antenna or contact of RFID tag 126, thereby providing enough power for RFID tag 126 to respond properly. On the other hand, active RFID tags and battery-assisted passive RFID tags (or semi-passive RFID tags) require a battery or other suitable power source. In battery-assisted passive RFID tags, a battery is employed to provide power for operation of the chip but not for communicating with RF transceiver antenna 150. The powered (active and semi-passive) RFID tags typically have longer operating ranges and greater capacity for data storage than passive RFID tags, but cost more and may have much shorter operating lives. The physical dimensions of a passive or active RFID tag may be in the micron or millimeter range. Typically, a passive RFID tag will be smaller than an active RFID tag.

RFID tag 126 and RF transceiver antenna 150 may operate within any suitable range of radio frequencies, including low-frequency or LF (typically considered as including the range of approximately 125-134 kHz), high-frequency or HF (typically 13.56 MHz or thereabouts), ultra-high frequency or UHF (typically considered as including the range of approximately 868-956 MHz) and microwave (for example, 2450 MHz). Each frequency or range of frequencies may have advantages or disadvantages depending on the particular implementation, as well as factors such as intended read range, operating environment, power requirements, costs of materials and fabrication, geometry, and the like. For purposes of the implementations disclosed herein, the frequency utilized for operation is one that is compatible with close-range, error-free communication, i.e., typically in the range of a few millimeters as previously noted.

The chip provided with RFID tag 126 may have read-write or read-only capability. When equipped with a read-write chip, new information can be added to RFID tag 126 or written over existing information. When equipped with a read-only chip, the information stored by RFID tag 126 cannot be changed unless the chip is reprogrammed. As appreciated by persons skilled in the art, the read-only chip of RFID tag 126 may include electrically erasable programmable read-only memory (EEPROM).

The data recorded by and stored on RFID tag 126 includes enough information to uniquely identify the sample residing in sample container 110 so that sample container 110 and/or its sample can be discriminated from other sample containers 110 and/or their respective samples. Generally, the code is long enough to enable each RFID tag 126 employed in a given system or procedure to have a unique identity for purposes of tracking through the system, correlation with other data, and the like. As a few examples, the size of the code may be 64 bits or 96 bits, although in other implementations the code may be larger or smaller. In the case where the code is employed simply as a unique identifier for a sample contained in a sample container 110, the code may be associated with an address in a remote memory where more detailed information regarding the sample has been stored, such as in a database stored on a computer provided with or communicating with sample handling system 100. For example, once the code has been read by RF transceiver antenna 150, the code may then used to search the database for more detailed information specifically relating to the individual sample identified by the code. The types of information with which the code may be associated may depend on many factors, such as the type of analysis or analyses to be performed on samples or the types of analytical instrumentation to be employed. The types of information may include, but are not limited to, the composition and properties of the sample (to the extent known), the origin of the sample (for example, a particular test site, specimen, patient, or the like), the date and time the sample was taken or prepared, the conditions under which the sample was prepared, the types of reagents, solvents, additives or chemical labels combined with the sample, the position (for example, row/column) of the sample container 110 within an array of sample containers 110, the identity of the particular group of sample containers 110 with which the sample container 110 is arranged (for example, a vial rack or tray, multi-well plate, or the like), and the like. Depending on the storage capability of RFID tag 126, one or more of these types of data may be directly stored in RFID tag 126 along with its identification code.

Figure 2:
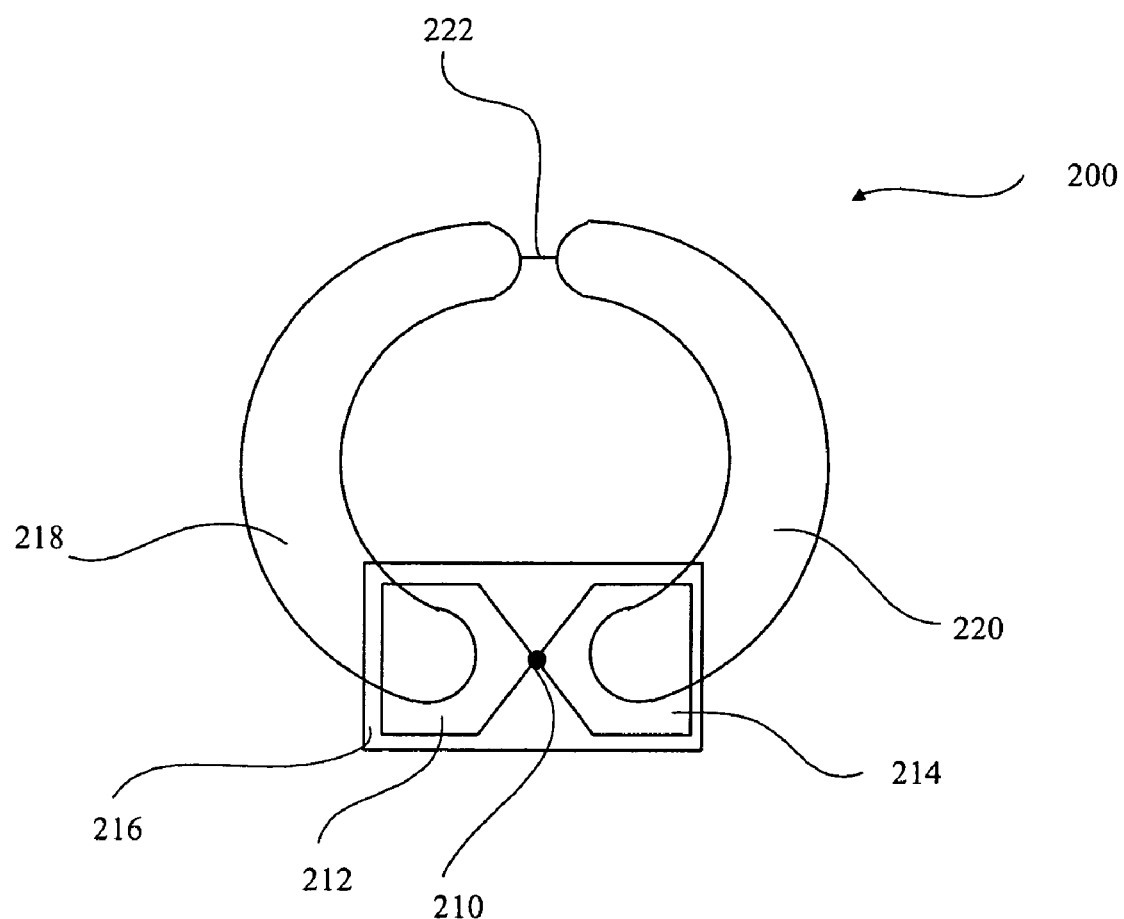
FIG. 2 is a top plan view of an RFID tag provided according to an example of one implementation.

FIG. 2 illustrates one example of an RFID tag 200 that may be utilized in conjunction with implementations described herein. RFID tag 200 includes a microchip 210 in which data including the unique identifier code, and alternatively other data as well, may be recorded and stored. One or more electrically conductive members 212 and 214 may be connected in electrical communication with microchip 210. In the illustrated example, two conductive members 212 and 214 are utilized and are provided in the form of flat metal plates. Conductive members 212 and 214 are attached to a substrate 216, which may be non-conductive. Microchip 210 is attached to conductive members 212 and 214 or directly to substrate 216 between conductive members 212 and 214. As shown in FIG. 2, conductive members 212 and 214 may be shaped such that RFID tag 200 may be characterized as having a bow-tie configuration. One or more antennas 218 and 220 may be connected to conductive members 218 and 220, respectively. Antennas 218 and 220 may have arcuate shapes such as substantially semicircular shapes. A thin conductive strip 222 may interconnect the ends of antennas 218 and 220 opposite to conductive members 212 and 214 to prevent static charge buildup that might damage microchip 210. Antennas 218 and 220 may be centered relative to axis 123 (FIG. 1). In alternative implementations, conductive members 212 and 214 may themselves serve as the antennas for RFID tag 200, in which case antennas 218 and 220 are not needed. An RFID tag 200 configured as illustrated in FIG. 2 may be particularly advantageous when operating at UHF.

Figure 3:
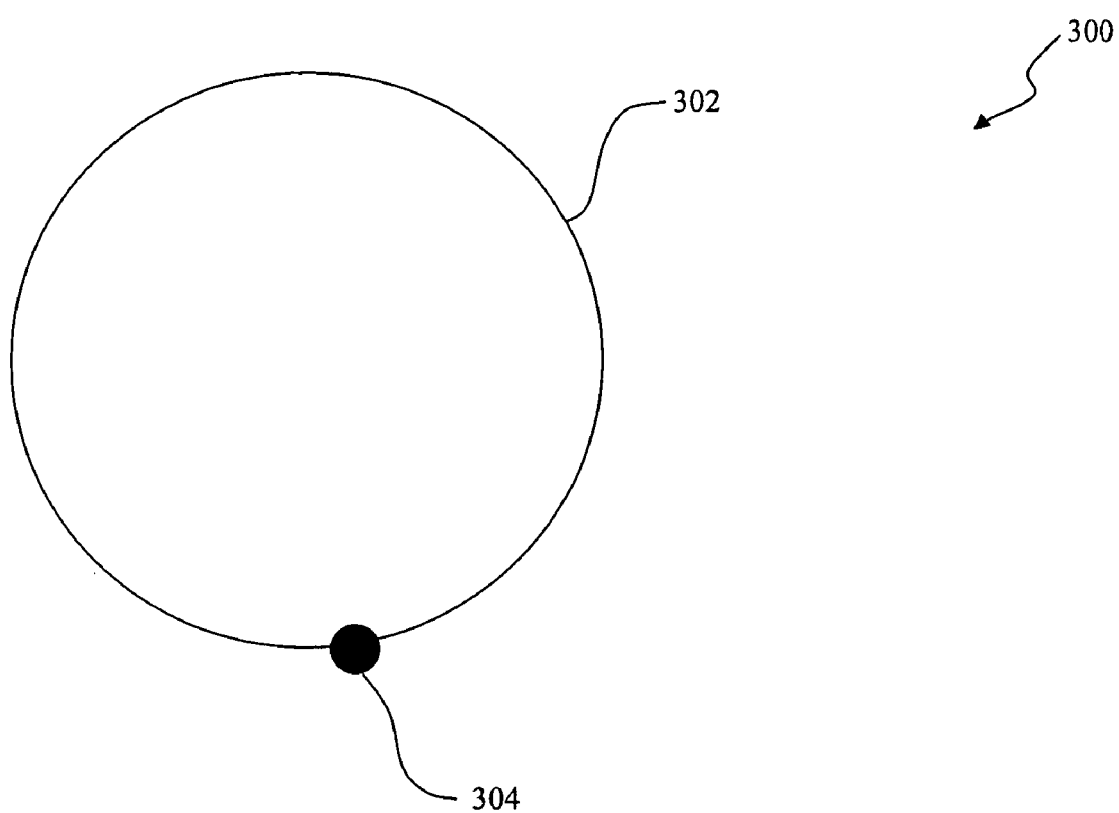
FIG. 3 is a top plan view of an RFID tag provided according to an example of another implementation.

FIG. 3 illustrates another example of an RFID tag 300 that may be utilized in conjunction with implementations described herein. RFID tag 300 generally has an annular, ring, or loop configuration. In some implementations, as shown for example in FIG. 1, RFID tag 126 may have a loop configuration similar to RFID tag 300 shown in FIG. 3, and may be utilized in conjunction with an annular RF receiver antenna 150 (FIG. 1). In these implementations, RF receiver antenna 150 and RFID tag 126 are concentric with sample probe 134 and sample container 110, which may increase the selectivity of the RFID system as previously noted. As shown by example in FIG. 3, RFID tag 300 may include a coiled antenna 302 attached by any suitable means to a microchip 304. Antenna 302 may include one or more loops of conductive wire, ribbon or other suitable material. Antenna 302 may be coated with or enclosed by an insulating material if appropriate. An RFID tag 300 configured as illustrated in FIG. 3 may be particularly advantageous when operating at frequencies lower than UHF such as, for example, HF.

Figure 4:
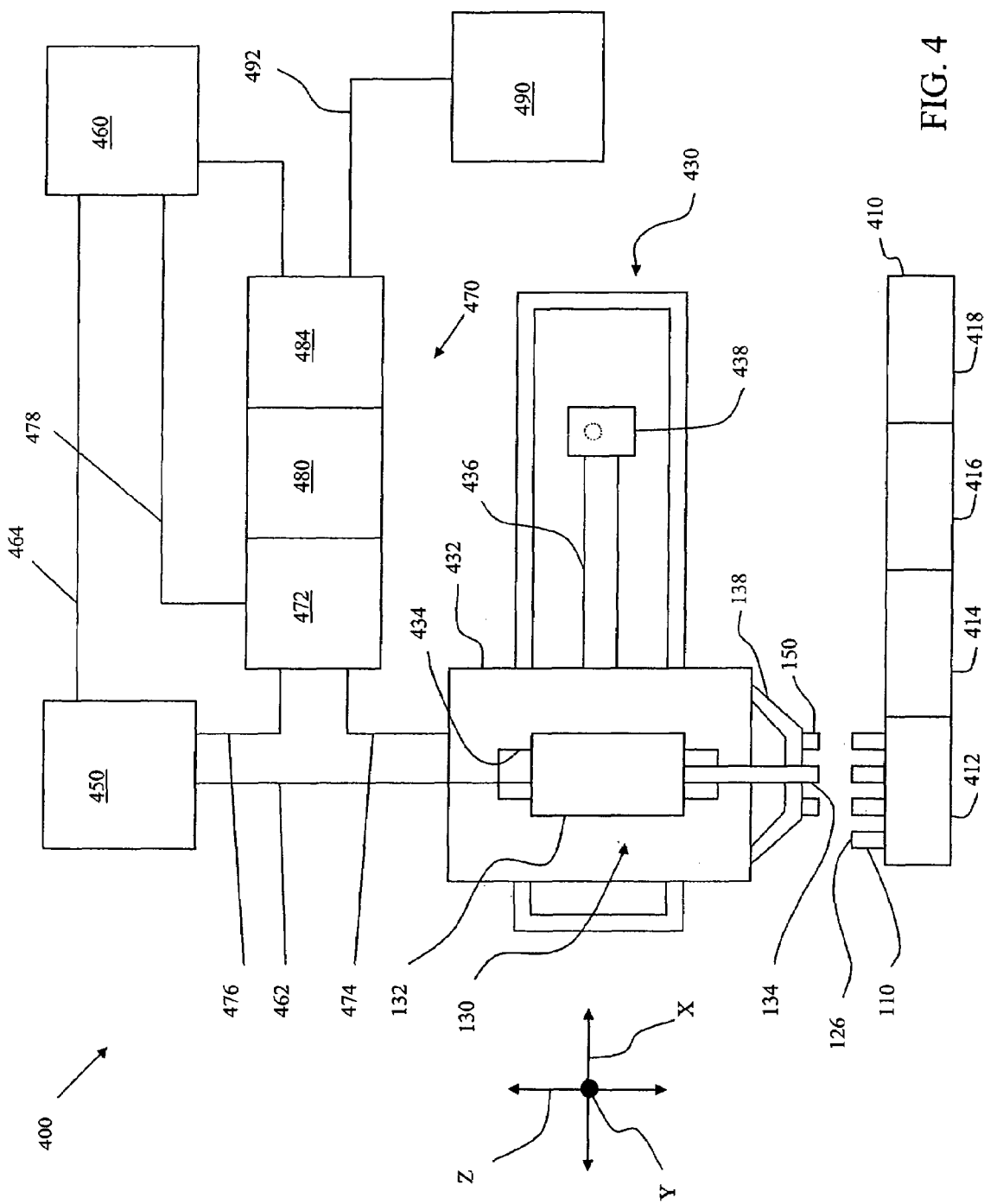
FIG. 4 is a schematic view of a sample handling apparatus or system and related components according to an example of one implementation.

FIG. 4 schematically illustrates an example of an automated sample handling apparatus or system 400 that includes the RFID functionality described above. Sample handling system 400 may include a sample holding assembly 410 that may in turn include one or more sample holding modules 412, 414, 416 and 418. While four sample holding modules 412, 414, 416 and 418 are specifically illustrated, more or less may be provided. Sample holding modules 412, 414, 416 and 418 may be provided in the form of racks or plates that include an array of apertures in which sample containers 110 can be mounted, typically in an upright (vertical) fashion. Sample containers 110 may be configured in the manner illustrated in FIG. 1. Alternatively, or additionally, sample holding assembly 410 may include a tray that supports the bottoms of sample containers 110 or sample holding modules 412, 414, 416 and 418. As another alternative, sample holding modules 412, 414, 416 and 418 may be provided in the form of multi-well plates, such as microtitre plates, in which sample containers 110 are formed as an array of wells or depressions in blocks of suitable material (for example, plastic or quartz). Still further, while in the presently described implementation sample holding assembly 410 provides for a generally rectilinear array (for example, rows and columns) of sample containers 110, it is readily appreciated that in other implementations sample holding assembly 410 may include a carousel that provides a rotary arrangement of sample containers 110.

Sample handling apparatus 400 may additionally include a mobile sampling assembly such as a robotic assembly 430. Robotic assembly 430 supports a movable member 132 such as a sample probe mounting device or carriage device, which may be configured as a sample probe device 130 and include a sample probe 134 as described above in conjunction with FIG. 1. As indicated schematically in FIG. 4 by arbitrarily designated X-, Y- and Z-axes, robotic assembly 430 is capable of moving sample probe 134 along one, two, or three dimensions (and typically at least two dimensions) as needed for positioning sample probe 134 into operational alignment with each sample container 110 or selected sample containers 110 that have been loaded into sample handling system 400. By this configuration, sample handling apparatus 400 is able to transfer selected samples (or portions of samples) to and/or from corresponding sample containers 110 in the case where sample probe 134 is a sample conduit. In the case where sample probe 134 is a probe of the analyzing, measuring, sensing, or detecting type, sample handling apparatus 400 is able to move this type of probe into and/or out from selected sample containers 110 when needed. In some implementations, sample handling apparatus 400 may include both probe of the sample-transferring type and probes of the analytical function type, and an RF transceiving antenna 150 may be provided in cooperation with one or both types of probes.

Sample probe device 130 is movably connected to another movable member 432 so as to be movable within a guide means such as a track 434 of movable member 432 along the Z-axis. In alternative implementations, sample probe 134 may itself be movable relative to a mounting structure of robotic assembly 430. Movable member 432 in turn is movably connected to a guide means such as an arm 436 or similar structure such that movable member 432 is movable along the X-axis. Arm 436 in turn is movably connected to another guide means such as an arm 438 such that arm 436 is movable along the Y-axis. Motors or actuators (not shown) responsible for the movement of these components in the various directions may be programmed so that sample probe 134 is positionable over designated sample containers 110 according to any desired sequence.

Sample probe 134 may communicate with other fluid circuitry typically provided with sample handling system 400. In FIG. 4, the other fluid circuitry is generally represented by block 450 and may include, for example, valves, tubing, sample loops, pumps, solvent and reagent reservoirs, rinsing stations, dilution modules, mixing chambers, waste receptacles, and the like as is readily appreciated by persons skilled in the art. Fluid communications between fluid circuitry 450 and sample probe 134, and between fluid circuitry 450 and any analytical instrument or instruments 460 that may be provided, are schematically depicted by lines 462 and 464, respectively.

Sample handling system 400 may further include electronic circuitry 470 for controlling the various operations of sample handling system 400. Electronic circuitry 470 may include hardware control circuitry 472 that is conventionally associated with sample preparation and liquid handling instrumentation. For example, hardware control circuitry 472 may control the operations of the various components of robotic assembly 430 and fluid circuitry 450. As another example, hardware control circuitry 472 may control the sequential injections of samples into analytical instrument 460 or combination of analytical instruments such as, for example, those associated with chromatography, spectroscopy, mass spectrometry, nuclear magnetic resonance spectrometry, calorimetry, and the like. Accordingly, hardware control circuitry 472 is schematically illustrated as electrically communicating with robotic assembly 430, fluid circuitry 450, and analytical instrument 460 via lines 474, 476, and 478, respectively. Electronic circuitry 470 may be programmable for all such purposes, such as through the execution of software and/or in response to user input via a suitable peripheral device.

In the example illustrated in FIG. 4, electronic circuitry 470 is shown to also include an RF signal processing circuit 480 that communicates with RF transceiver antenna 150 to receive code-bearing signals detected from RFID tags 126 and process the signals as digital information. Particularly in implementations in which RFID tags 126 are passive, RF signal processing circuit 480 may function to produce the RF signal that is transmitted by RF transceiver antenna 150 to activate RFID tags 126 in order to acquire their respective coded information. RF signal processing circuit 480 may be interfaced by any suitable means with hardware control circuitry 472, as well as with any data acquisition software provided with analytical instrument 460, so that their respective operations and functions are coordinated as needed. Electronic circuitry 470 is further shown to include memory 484 for storing a database containing information associated with the codes transmitted by RFID tags 126. Memory 484 may be provided in any suitable format and may be interfaced with removable storage media.

It will be understood that hardware control circuitry 472, RF signal processing circuit 480, and sample information-containing memory 484 are illustrated in FIG. 4 as being integrated as a single schematic block (electronic circuitry 470) by way of example only. The various functions described here may be implemented in separate modules, including computers, function- or application-specific electronic processing devices, remote servers, and the like. As one example, a programming station 490 by which codes are recorded in RFID tags 126 may also be configured to allow a user to initially populate the database containing information associated with each code. In this implementation, the contents of the database may thereafter be transferred to memory 484 in electronic circuitry 470 via a suitable communication line 492 or by removing storage media from programming station 490 and then loading the media into memory 484. Moreover, communications between electronic circuitry 470 and robotic assembly 430, fluid circuitry 450, analytical instrument 460, and programming station 490 are represented by lines 474, 476, 478, and 492, respectively, for the sake of simplicity. In practice, these lines 474, 476, 478, and 492 may represent one or more signal paths as needed for communications, and may represent hard wiring and/or airborne, wireless signals.

Figure 5:
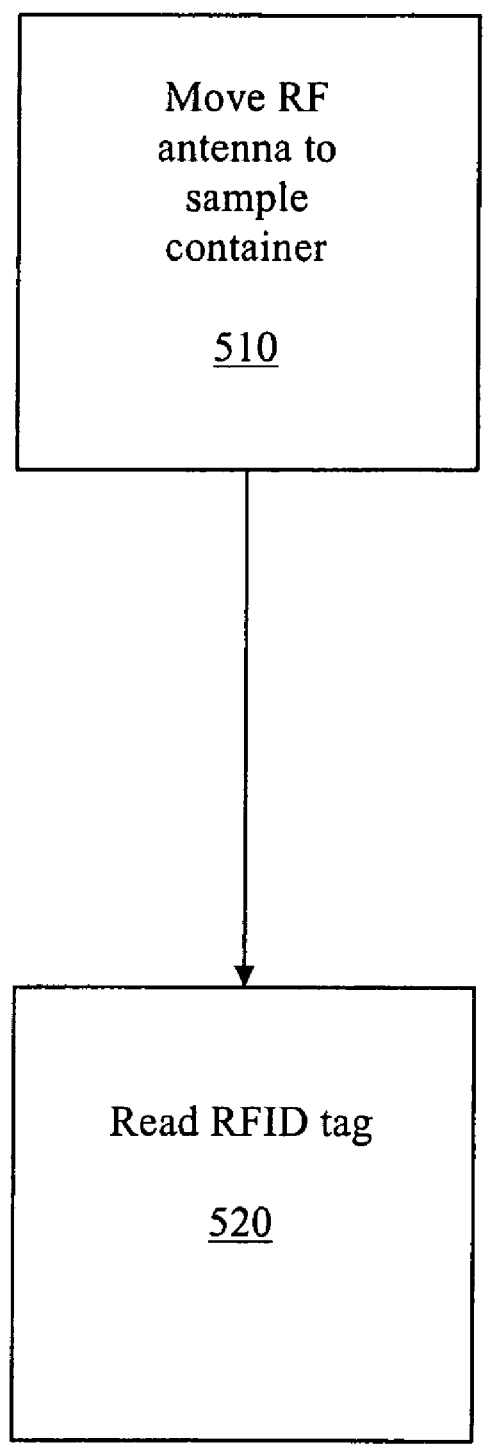
FIG. 5 is a flow diagram illustrating a method for uniquely identifying an analytical sample according to an example of one implementation.

Referring now to FIG. 5, and with reference to the various implementations described above and illustrated in FIGS. 1-4, an example of a method for uniquely identifying an analytical sample will now be described. A sample container 110 that includes an RFID tag 126 (or 200, or 300) is provided. Sample container 110 and its RFID tag 126 may be configured or designed in accordance with one or more of the examples of implementations described above. RFID tag 126 contains information relating to a sample contained in sample container 110. As described above, the sample information may include a code that serves as a unique identifier for the sample and/or the sample container 110 in which the sample resides. The sample information may additionally include other data relating to the sample, such as features, properties, constituents, origin, conditions under which the sample was prepared, and the like as described above. In some implementations of the method, a plurality of sample containers 110 equipped with RFID tags 126 are provided. The plurality of sample containers 110 may be arranged in an ordered array such the respective positions of the sample containers 110 can be defined. A sample probe device 130 that includes a sample probe 134 and an RF transceiver antenna 150 is also provided. Sample probe device 130 may be configured or designed in accordance with one or more of the implementations described above. The plurality of sample containers 110 may be positioned with a sample handling apparatus or system 100 or 400 that has one or more automated features or components such as described above.

At block 510 in FIG. 5, sample probe device 130 is moved into proximity with a sample container 110. That is, sample probe device 130 is moved into a position relative to sample container 110 such that RF transceiver antenna 150 is close enough to RFID tag 126 of sample container 110 to enable the coupling of RF energy between RF transceiver antenna 150 and RFID tag 126. In other words, as a result of movement of sample probe device 130, RFID tag 126 falls within the RF transmission range of sample probe device 130. This range is close enough to ensure that RF transceiver antenna 150 communicates with the intended sample container 110 and not with any other neighboring sample container 110, and without interference with any other neighboring sample container 110. In particularly desirable implementations, this range is a close range, for example 0-10 mm. In some implementations such as described above, the position into which sample probe device 130 is moved relative to sample container 110 is a position directly above sample container 110 where RF transceiver antenna 150 is generally aligned with RFID tag 126. RF transceiver antenna 150 broadcasts an activation or query signal so as to be able to scan for one or more sample containers 110. RF transceiver antenna 150 may broadcast its signal on a continuous basis or at regular intervals. Alternatively, the broadcasts by RF transceiver antenna 150 may be coordinated or synchronized with the movement of sample probe device 130 (and thus RF transceiver antenna 150), such that RF transceiver antenna 150 transmits its signal only upon reaching its final position relative to the targeted sample container 110. In implementations where a plurality of sample containers 110 are provided, the movement of sample probe device 130 may follow a predetermined or programmed path from one sample container 110 to another. For example, sample probe device 130 may be coupled to a programmable robotic assembly 430 provided with a sample handling apparatus 400, as described above.

At block 520 in FIG. 5, RF transceiver antenna 150 reads sample data stored by the RFID tag 126 of the target sample container 110. As a result, the sample contained in sample container 110 is identified and, consequently, may be readily distinguished from other samples that are the subjects of the sample handling, preparation and/or analysis processes being performed. Depending on the amount and types of sample data stored on a given RFID tag 126 interrogated by RF transceiver antenna 150, RF transceiver antenna 150 may forward the data acquired to suitable electronic circuitry such as a microprocessor (operating, for example, within electronic circuitry 470 shown in FIG. 4). The electronic circuitry may interface with a database to associate the sample data acquired by RF transceiver antenna 150 with additional (and typically more detailed) data pertaining to the sample that has just been identified. The accessing of a database, look-up table, or the like is particularly useful in implementations where the sample data retrieved from an RFID tag 126 is merely a code that uniquely identifies the sample. In some implementations, once an RFID tag 126 of a sample container 110 has been read, the sample may be transferred to one or more analytical instruments 460 for analysis.

In some implementations, the method just described and illustrated in FIG. 5 may constitute a single iteration, and hence may be repeated for other sample containers 110 that are being processed.

In some implementations, RF transceiver antenna 150 may be utilized to determine whether a particular position within or relative to a sample handling apparatus or system 100 or 400 is occupied by a sample container 110, or whether a sample container 110 is missing from that particular position, or whether a sample container 110 occupying that particular position lacks an RFID tag 126 or has a defective RFID tag 126. The RF-related components as disclosed herein allow such operations even in the presence of other RFID-tagged sample containers occupying neighboring positions in close proximity to the presently targeted position. In still other implementations, RF transceiver antenna 150 may be utilized to scan an entire array of sample containers 110 (see, for instance, sample holding assembly 410 and associated components illustrated in FIG. 4), not only to acquire sample data but also to compile a list of sample containers 110 that are present or absent at the various positions of the array. This scan may or may not involve momentarily stopping RF transceiver antenna 150 over each target sample container 110 or sample container site. Again, the RF-related components as disclosed herein allow such operations to be carried out accurately at each targeted position without neighboring sample containers 110 interfering with the operations.

In some implementations, sample probe 132 may perform an analytical function or operation while located at a given sample container 110, and this function or operation may be executed before, during, or after RF transceiver antenna 150 read the data from RFID tag 126. Examples of analytical functions or operations that may be performed by sample probe 132 may include analytical, detecting, or measuring tasks such as, optical detection, temperature measurement, or the like.

From the foregoing, it may be seen that the implementations disclosed herein can provide advantages over barcode technology and other previous techniques for identifying samples. For example, the reader, such as RF transceiver antenna 150, does not require a line of sight with RFID tag 126 in order to detect the information stored by RFID tag 126, whereas barcode scanners need to "see" a barcode in order to read it. Moreover, RFID tags 126 are insensitive to orientation with a reader, whereas a barcode must be optically aligned with a barcode scanner. RFID tags 126 allow for individual sample containers 110 to have unique identifiers and can quickly identify several individual samples either simultaneously or sequentially, whereas the typical barcode provides only an identification of a manufacturer and product. In closely arranged groupings of sample containers 110, RF transceiver antenna 150 and a selected RFID tag 126 can communicate without interference or error due to the proximity of other tagged sample containers 110. RFID tags 126 are much more robust than barcode labels, and have much longer useful lives. RFID tags 126 are much more resistant to potential laboratory mishaps such as smearing, solvent exposure, abrasion, obstruction, and the like. RFID tags 126 are programmable and may further be reprogrammable. The same RFID tag 126 can be recoded with new information when desired. An RFID tag 126 in many implementations can store much more information than is possible with a barcode label. The RFID tags 126 in combination with RF-based readers may be easily integrated into existing sample handling systems without unduly affecting any other pre-existing, more conventional operations of such systems. Because an RF interrogation element such as an antenna can be easily incorporated into a moving component such as a device or assembly supporting a sample conduit, the implementations disclosed herein introduce the concept of moving the RF interrogation element to sample containers 110. Individual sample containers 110 do not need to be moved to reading or scanning stations or the like.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample handling apparatus comprising:
   a robotic assembly comprising a movable member;
   a sample probe device mounted to and movable with the movable member, the sample probe device comprising a sample probe;
   a sample container accessible by the sample probe and comprising a first structure including an open end and enclosing an interior, a second structure mounted to the first structure at the open end, and an RFID tag positioned near the open end; and
   an RF transceiver antenna mounted to the movable member, whereby the RF transceiver antenna is movable into proximity with the RFID tag for communicating therewith.

2. The apparatus of claim 1, wherein the RF transceiver antenna is substantially centered about the sample probe, and the RFID tag comprises an RF transmitting component substantially centered about a central axis of the sample container.

3. The apparatus of claim 2, further wherein the sample probe device comprises a sample probe guide, the sample probe extends through the guide, and the RF transceiver antenna is mounted to the guide.

4. The apparatus of claim 3, wherein the guide is an annular sample probe guide positioned with the movable member and coaxially disposed about the sample probe.

5. The apparatus of claim 4, wherein the first structure of the sample container extends along the central axis and the RF transmitting component annularly disposed about the central axis.

6. The apparatus of claim 2, wherein the RF transmitting component of the RFID tag is concentrically disposed about the central axis.

7. The apparatus of claim 1, wherein the sample probe is a hollow conduit.

8. A method for uniquely identifying an object, comprising:
   moving a sample probe device comprising an RF transceiver antenna and a sample probe into proximity with a sample container, which includes a first structure enclosing an interior and having an open end, and a second structure mounted to the first structure at the open end; and
   using the RF transceiver antenna to read a code stored by an RFID tag mounted to the first structure and includes an RF transmitting component coaxially disposed about a central axis of the first structure, whereby the object can be identified from the code.

9. The method according to claim 8, comprising, after reading the code, associating the code with information relating to the identified sample.

10. The method according to claim 8, comprising using the sample probe to transfer a sample to or from the sample container.

11. The method according to claim 8, comprising using the sample probe to perform an analytical function in the sample container.

12. The method according to claim 8, comprising using the RF transceiver antenna to determine whether the sample container is present at a selected location.

13. The method according to claim 8, comprising inserting the sample probe through a closure member mounted to the sample container and into the sample container.

14. The method according to claim 8, wherein the sample container is a target sample container positioned proximate to one or more neighboring sample containers including respective RFID tags, and using the RF transceiver antenna comprises communicating with the RFID tag of the target sample container without interference from RFID tags of the one or more neighboring sample containers.

15. The method of claim 8, wherein moving includes moving the RF transceiver antenna into proximity with the RF transmitting component.

16. The method of claim 8, wherein moving includes moving the sample probe into alignment with a central axis of the first structure.

17. The method of claim 8, wherein the sample probe device includes an annular sample probe guide positioned with the movable member, the sample probe extends through the sample probe guide such that the sample probe guide is coaxially disposed about the sample probe, and the RF transceiver antenna is mounted to the sample probe guide, and further wherein moving includes moving the sample probe guide into proximity with the RFID tag.

18. The method of claim 8, wherein the object being identified is a sample contained in the sample container or the sample container.

19. A sample container comprising:
   a first structure extending along a central axis, the first structure enclosing an interior and including an open end;
   a second structure mounted to the first structure at the open end; and
   an RFID tag including an RF transmitting component annularly disposed about the central axis.

20. The container of claim 19, wherein the interior enclosed by the first structure has a volume ranging from approximately 0.1 mL to approximately 1000 mL.

21. The container of claim 19, wherein the RFID tag is positioned with the first structure.

22. The container of claim 19, wherein the RFID tag is positioned with the second structure, which comprises a cap mounted to the first structure at the open end.

23. The container of claim 22, comprising a closure member mounted to the first structure at the open end, whereby the interior is isolated from an environment external to the first structure.

24. The container of claim 19, comprising a closure member mounted to the first structure at the open end whereby the interior is isolated from an environment external to the first structure, and wherein the second structure comprises a cap mounted to the first structure at the open end, and the cap includes an aperture providing access to the closure member from the external environment.

25. A sample container comprising:
   a container structure extending along a central axis and having an open end;
   a cap mounted to the container structure at the open end and including a closure member isolating the container structure from an environment external to the cap, the cap having an aperture located at the central axis and providing access to the closure member from the external environment; and
   an RFID tag including an RF transmitting component substantially centered about the central axis.

* * * * *